United States Patent [19]
Vatterott

[11] Patent Number: 5,394,567
[45] Date of Patent: Mar. 7, 1995

[54] UNIVERSAL SIDE SHIELD

[76] Inventor: Ralph O. Vatterott, 11185 Golf Crest Dr., St. Louis, Mo. 63126

[21] Appl. No.: 207,359

[22] Filed: Mar. 7, 1994

[51] Int. Cl.$^6$ .............................................. A61F 9/02
[52] U.S. Cl. .............................................. 2/449; 2/13
[58] Field of Search ............ 2/449, 448, 451, 13; 351/47, 44, 48, 123

[56] References Cited

U.S. PATENT DOCUMENTS

| | | | |
|---|---|---|---|
| 1,193,340 | 8/1916 | Bader | 2/449 |
| 1,340,701 | 5/1920 | Day | 2/449 |
| 1,706,682 | 3/1929 | Takacs | 2/13 |
| 2,253,101 | 8/1941 | Thoreson | 2/13 |
| 2,281,129 | 4/1942 | Wolff | 2/13 |
| 2,858,539 | 11/1958 | Carlson | 2/13 |
| 3,204,252 | 9/1965 | Herrington, Sr. | 2/13 |
| 3,505,679 | 4/1970 | Bennett | 2/13 |
| 3,596,290 | 8/1971 | Kennedy | 2/13 |
| 3,932,031 | 1/1976 | Johnston | 351/47 |
| 4,298,991 | 11/1981 | Recenello | 2/13 |
| 4,751,746 | 6/1988 | Rustin | 2/449 X |
| 5,113,529 | 5/1992 | Carr | 2/13 |
| 5,206,956 | 5/1993 | Olson | 2/13 |

Primary Examiner—Peter Nerbun
Attorney, Agent, or Firm—Senniger, Powers, Leavitt & Roedel

[57] ABSTRACT

A shield for application to a temple bar of a pair of glasses functions to shield the user's eye at that side. The shield comprises an elongate relatively thin rigid plastic plate member which as applied to the temple bar lies generally flat against the respective side of the user's head and extends between the frame and the respective ear of the user. The plate member has a forward generally flat panel positionable on the outside of the temple bar, an intermediate generally flat transition panel angled rearwardly and inwardly from the forward panel and having an opening therein for the temple bar, and a rearward generally flat panel extending rearward from the intermediate transition panel on the inside of the temple bar as the shield is applied to the bar. The rearward panel has a clip for clipping the rearward panel on the temple bar. The side shield further comprises an inwardly extending flange at a forward edge of the forward panel. The flange extends in front of the pair of glasses at the side thereof. The flange is of such width and so configured as not to interfere with the user's vision. The flange acts to hold the shield against rearward movement on the temple bar when the bar is in position extending from the frame of the pair of glasses. The flange moves out from in front of the frame when the bar is swung closed.

13 Claims, 2 Drawing Sheets

UNIVERSAL SIDE SHIELD

BACKGROUND OF THE INVENTION

This invention relates generally to eyewear, and, more particularly, to protective side shields which may be mounted on the temple bars of a pair of glasses for shielding the wearer's eyes from wind, dust and debris.

Side shields have been developed to reduce the risk of injury to the eyes of a person who wears glasses, particularly in environments where there is a significant danger that particles may intrude into the areas behind the lenses of the glasses. While persons not wearing corrective lenses may find safety goggles readily usable, persons who must wear corrective lenses have difficulty wearing them with safety goggles. Safety goggles can be constructed to have special corrective lenses, thereby eliminating the need for eye glasses, but such goggles are expensive, especially for a person who has only an occasional use for them.

Prior side shield designs are generally adequate for protecting a person wearing glasses from dust and debris entering from the side. However, such designs do not protect the wearer from debris falling from above. Moreover, in the event the wearer is struck by a heavier object, the prior art designs are not effective in dispersing the forces of impact, which may result in damage to the eye socket of the wearer.

Further, some prior side shields cannot be folded with the glasses. As a result, the shields must be removed from the glasses before the glasses can be stored. Since the side shields are thin and small, they are often lost so removed.

SUMMARY OF THE INVENTION

Among the several objects and features of the present invention may be noted the provision of a side shield which effectively protects the eyes of the wearer from dust and debris; the provision of such a side shield which provides protection from debris falling from above; the provision of such a side shield which is easy to install on any pair of glasses having a temple bar notwithstanding the size or location of the temple bar relative to the frame; the provision of such a side shield which is designed to maintain its proper position on the temple bar; the provision of such a side shield which mounts on glasses without distorting the peripheral vision of the wearer; the provision of such a side shield is designed to fold with the temple bar for storage with the glasses; the provision of such a side shield which utilizes the wearer's face upon a side impact to support the shield and disperse the forces of impact; and the provision of such an edge guard which is relatively inexpensive to manufacture.

Generally, a side shield of this invention functions to shield the user's eye at the side of the pair of glasses to which the shield is applied. The side shield is applied to a temple bar of a pair of glasses comprising a frame and left and right temple bars each pivotally interconnected at one end constituting its forward end to the frame at a respective side of the frame. The shield comprises an elongate relatively thin rigid plastic plate member which as applied to a temple bar lies generally flat against the respective side of the user's head extending between the frame and the respective ear of the user. The plate member has a forward generally flat panel having a forward edge and a rearward edge and positionable on the outside of the temple bar and an intermediate generally flat transition panel angled rearwardly and inwardly from the rearward edge of the forward panel and having an opening therein for the temple bar. The intermediate transition panel has a rearward edge which is on the inside of the respective temple bar as the shield is applied to its bar. The plate member further comprises a rearward generally flat panel extending rearward from the rearward edge of the intermediate transition panel on the inside of the temple bar as the shield is applied to the bar. The rearward panel has clip means for clipping the rearward panel on the temple bar. The side shield further includes an inwardly extending flange at the forward edge of the forward panel. The flange extends in front of the frame of the pair of glasses at the side thereof from the bar to which the shield is applied. The flange is of such width and so configured as not to interfere with the user's vision, and acts to hold the shield against rearward movement on the temple bar when the bar is in position extending from the frame. The flange moves out from in front of the frame when the bar is swung closed.

Other objects and features will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF A PREFERRED EMBODIMENT

Figure 1:
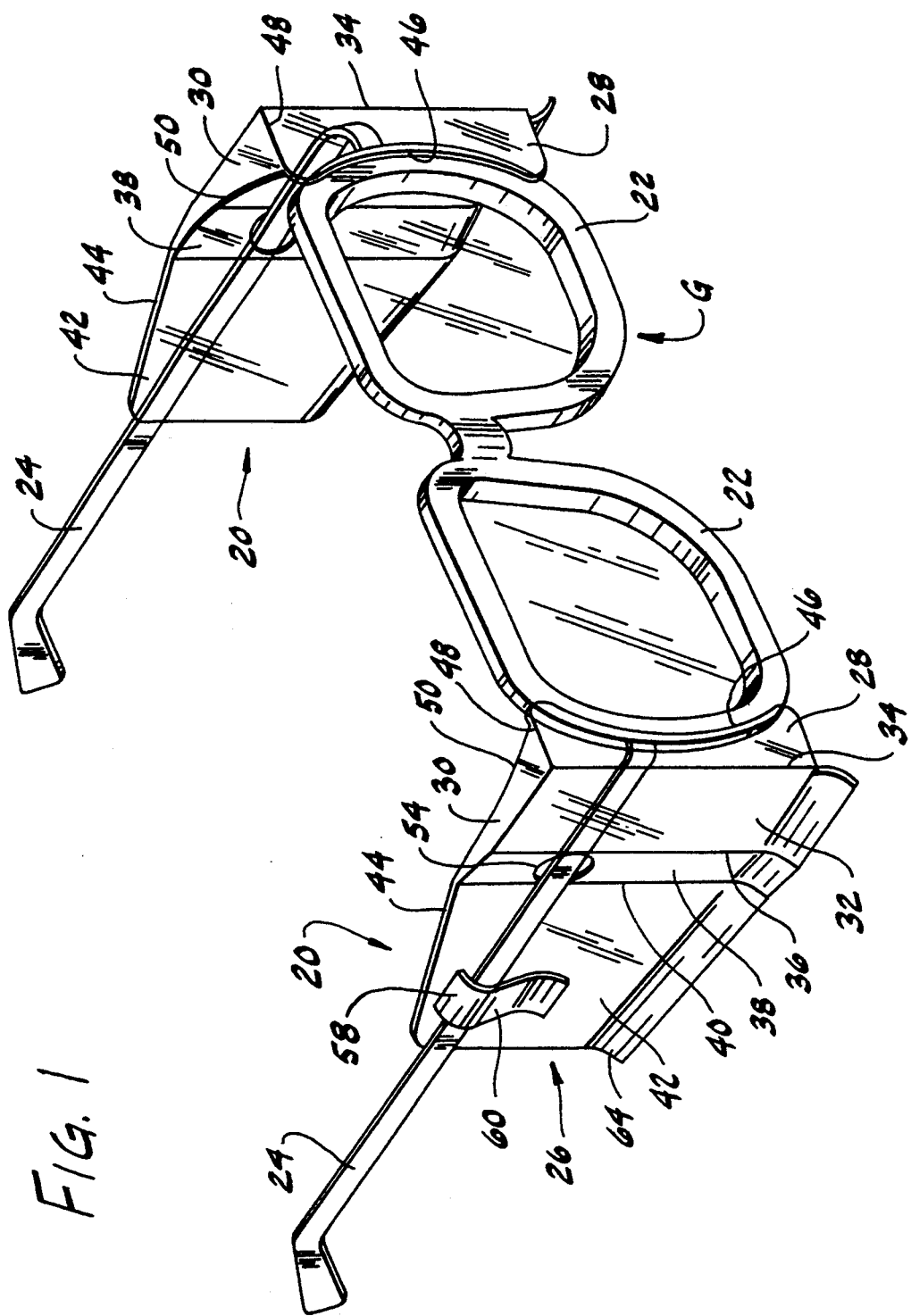
FIG. 1 is a perspective of a pair of side shields of this invention mounted to the temple bars of a pair of glasses.
Figure 2:
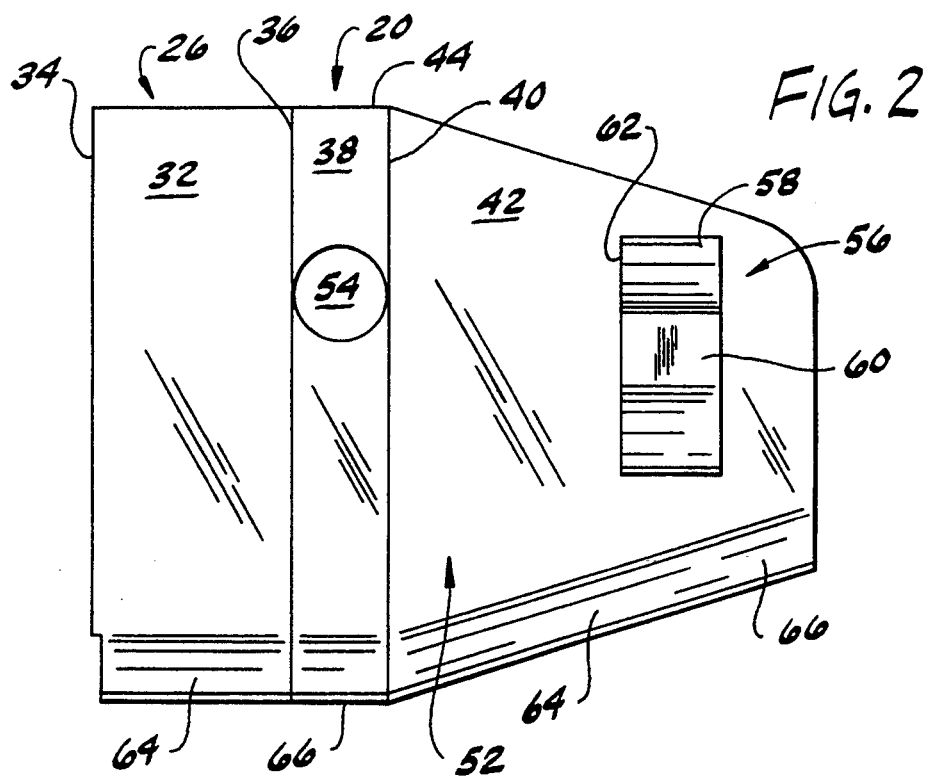
FIG. 2 is a side elevational view of a side shield of the present invention.

Referring now to FIG. 1 of the drawings, a pair of side shields of the present invention, each indicated generally at 20, are shown mounted on a pair of glasses G. As depicted, the eyeglasses G are of standard design, comprising a frame 22 and left and right temple bars, each indicated at 24, each pivotally interconnected at one end constituting its forward end to the frame at a respective side of the frame. As described in more detail hereinafter, the side shields 20 function to shield the user's eyes from airborne particles, flying debris and the like.

Each shield 20 comprises an elongate relatively thin rigid plastic plate member, generally depicted 26, an inwardly extending front flange 28, and an upper protection plate 30 extending between the plate member and the front flange. The plastic plate member 26 is preferably fabricated from a thin, substantially rigid plastic and lies generally flat against the respective side of the user's head as applied to a temple bar 24. The plate member 26 extends between the frame 22 and the respective ear of the user (not shown) and, as shown in FIG. 1, includes a forward generally flat panel 32 positioned on the outside of the temple bar 24 and having a forward edge 34 and a rearward edge 36, an intermediate generally flat transition panel 38 angled rearwardly and inwardly from the rearward edge 36 of the forward panel 32 and having a rearward edge 40 which is on the inside of the respective temple bar 24, and a rearward generally flat panel 42 extending rearward from the intermediate transition panel 38 on the inside of the temple bar. The plate member 26 further includes a generally horizontal upper edge 44 as the shield 20 is applied to the temple bar 24.

As shown in FIG. 1, the inwardly extending front flange 28 of the shield 20 extends from the forward edge 34 of the forward panel 32 to a position in front of the frame 22 (and preferably slightly overlapping the frame) of the eyeglasses G at the side thereof to effectively close the gap between the plate member 26 and the frame 22 of the glasses. The front flange 28 has an inner edge 46 which is generally concave to correspond with the arcuate shape of the eye frame of most glasses, and a generally horizontal upper edge 48 as the shield 20 is applied to the temple bar 24. The front flange 28 is preferably formed of the same plastic material as the plate member 26 and is of such a width and so configured as not to interfere with the user's vision.

Figure 3:
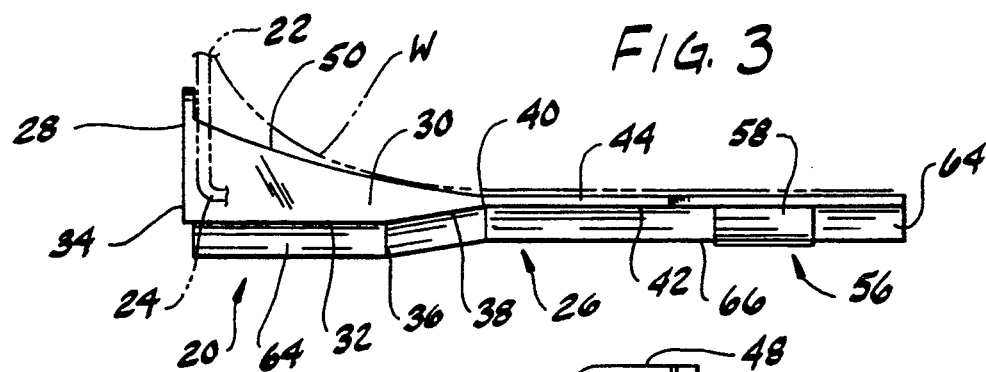
FIG. 3 is a top plan view of FIG. 2.

As shown in FIGS. 1 and 3, the upper protection plate 30 extends from the upper edge 44 of the plate member 26 to the upper edge 48 of the front flange 28. The upper protection plate 30 includes an inner edge 50 configured to correspond generally to the contour of the wearer's face, generally depicted at W in ghost lines, so that the upper plate 30 fits relatively snugly against the side of the wearer's head. Preferably, the upper protection plate 30 extends from the rearward edge 40 of the transition panel 38 to the front flange 28 of the shield 20, as shown in FIG. 3. Further, the inner edge 50 of the protection plate 30 is preferably integrally connected to the flange 28 at a position where the flange is in front of the frame 22 of the glasses G. This configuration minimizes the gap between the plate member 26 and the wearer's head W and the gap between the front flange 28 and the wearer's head to provide maximum protection against debris falling behind the lenses of the eyeglasses. It is to be understood that the upper protection plate 30 may extend from any portion of the plate member 26 to any portion of the front flange 28 without departing from the scope of this invention.

Figure 4:
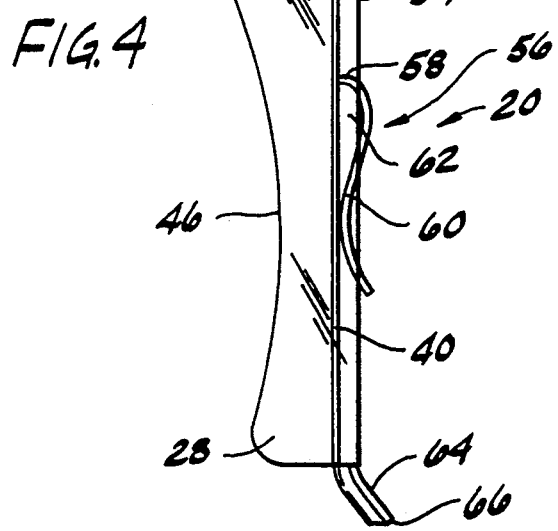
FIG. 4 is a front view showing an inwardly extending flange of the side shield of FIGS. 2 and 3.

Each side shield 20 is removably mounted on a respective temple bar 24 by means of a hole and clip arrangement, generally indicated at 52. The transition panel 38 of the plate member 26 is configured with an opening or hole 54 therein for receiving the temple bar 24 when the side shield 20 is mounted on the bar. The opening 54 in the transition panel 38 is sized to permit any temple bar 24 to fit therethrough. The location of the hole 54 in the transition panel 38 causes the periphery of the hole to contact the temple bar 24 and provide a friction fit for the temple bar. The rearward panel 42 of the rigid plate member 26 has clipping means in the form of a clip generally designated 56 for clipping the rearward panel to the temple bar 24. In the preferred embodiment, this clip 56 comprises a top wall portion 58 extending outwardly from the rearward panel 42 and a resilient leg portion 60 extending generally downwardly and inwardly from the top wall portion to the rearward panel to define in conjunction with the top wall portion 58 and rearward panel 42 an aperture (indicated at 62 in FIG. 4) for receiving the temple bar 24. The clip 56 is sized for releasably holding any temple bar 24 by applying a clamping force to the bar.

The aperture 62 of the clip 56 is co-linearly arranged with the opening 54 of the transition panel 38. This design enables the shield 20 to be mounted on any pair of spectacles having a temple bar 24 regardless of the thickness, width, or location of the temple bar relative to the frame 22 of the glasses. Thus, this method for mounting the side shield 20 is independent of the particular shape of the temple bar 24 and/or glasses G. Further, in the hole and clip mounting arrangement shown in the drawings at 52, the clip 56 is positioned on the flat rearward panel 42 of the plate member 26 rearwardly of the opening 54 in the transition panel 38. The flat rearward panel 42 is thus positioned between the temple bar 24 and the wearer's head W, and the clip 56 extends outwardly away from the wearer's head to provide a smooth, substantially flat surface for contacting the wearer's head.

To mount the side shield 20 on a temple bar 24 of a pair of glasses G, the temple bar is speared through the opening 54 in the transition panel 38 and the shield is slid rearwardly on the temple bar until the inwardly extending front flange 28 contacts the frame 22 of the glasses. The rigid plate member 26 is then clipped onto the temple bar 24 by means of the clip 56. The positive contact between the frame 22 of the glasses G and the front flange 28 of the shield 20 prevents the mounted shield from sliding further back on the temple bar 24. The clamping force exerted by the clip 56 and the friction fit of the temple bar 24 through the opening 54 in the transition panel 38 combine to prevent the shield 20 from sliding forwardly on the temple bar as, for example, when the wearer leans over.

The side shield 20 is able to fold with the temple bar 24 of the glasses G to a closed position for storage. As the temple bar 24 is pivoted to a folded position, the side shield 20 conjointly moves with the temple bar because the side shield is attached only to the bar, not the frame 22. The front flange 30 of the side shield 20 moves out from in front of the frame 22 and pivots away from the frame as the temple bar 24 is swung closed. Since the side shield 20 is able to be stored with the glasses G, the shield can be permanently affixed to a pair of glasses.

The side shield 20 is further constructed so that if a heavy object collides with the shield from the side of the shield, the force of impact is distributed over the face in an area below and behind the eye socket. To this end, the plate member 26 as applied to the temple bar 24 extends downwardly from the temple bar to a position below the eye socket of the wearer, and the plate member has a bottom margin 64 which extends from the forward panel 32 to the rearward panel 42, the latter of which is posterior of the eye socket. The bottom margin 64 of the plate member 26 flares outwardly away from the user's face (FIG. 3). When impacted by a heavy object, the side shield 20 uses the portion of the wearer's face which is in contact with the side shield, i.e., the portion of the wearer's face contiguous with the rearward panel 42, to distribute the force of impact. Thus, the impact force is distributed to an area located below and behind the eye socket. The outwardly projecting lip 66 of the bottom margin 64 insures that in the event of an impact a smooth surface contacts the wearer's face to reduce the risk of laceration.

In the preferred embodiment, the plate member 26, inwardly extending flange 28, and upper protection plate 30 of the side shield 20 are transparent. This permits the wearer to retain full peripheral vision while using the side shield 20. Furthermore, the forward panel 32 of the plate member 26 preferably extends rearwardly a distance sufficient to present a flat surface to the user's peripheral vision, thereby reducing distortion.

It should be noted that the side shield 20 or any part thereof can be tinted (i.e., the degree of transparency can be reduced) to diminish the glare of the sun. In this respect, the side shield 20 can also function as a visor to protect the eyes from the sun.

In a typical embodiment, the side shield 20 is approximately 2.75 inches in length and 2 inches high, and the forward panel 32 of the plate member 26 extends rearwardly approximately ⅜ in. from the front edge 34 of the forward panel. Further, the opening 54 in the transition panel 38 is approximately ⅜ in. in diameter to accommodate any size temple bar 24. It is to be understood that the dimensions of the side shield 20 can be varied without departing from the scope of this invention.

It will be observed, therefore, that the several objects and features of the present invention are achieved in the side shield disclosed herein. As shown in FIG. 1, the configuration of the side shield 20 provides protection from dust and debris entering from the side and, due to the upper protection plate 30, also protects against dust and debris entering from above. The side shield 20 is made of a transparent material and is constructed so as not to impede the peripheral vision of the wearer.

The hole and clip mounting arrangement 52 also makes the side shield 20 easy to install on any pair of glasses having a temple bar notwithstanding the size or location of the temple bar relative to the frame 22. This mounting arrangement 52 further enables the side shield 20 to fold with the temple bar 24 for storage with the glasses G. As mounted, the front flange 28 of the side shield 20 contacts the frame 22 of the pair of glasses G and maintains the side shield in proper position on the temple bar 24.

The configuration of the side shield 20 further uses the wearer's face in the event the side shield is struck by an object from the side to support the shield and disperse the force of impact to an area below and behind the eye socket.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A shield for application to a temple bar of spectacles comprising a frame and left and right temple bars each pivotally interconnected at one end constituting its forward end to the frame at a respective side of the frame, said shield as applied to a temple bar at one side of the spectacles functioning to shield the user's eye at that side, said shield comprising an elongate relatively thin rigid plastic plate member which as applied to a temple bar lies generally flat against the respective side of the user's head extending between the frame and the respective ear of the user, said plate member having a forward generally flat panel having a forward edge and a rearward edge and positionable on the outside of the temple bar, an intermediate generally flat transition panel angled rearwardly and inwardly from the rearward edge of the forward panel and having an opening therein for the temple bar, said transition panel having a rearward edge which is adapted to extend on the inside of the respective temple bar as the shield is applied to its bar, and a rearward generally flat panel extending rearward from the rearward edge of the intermediate transition panel and adapted to extend on the inside of the temple bar as the shield is applied to the bar, said rearward panel having clip means thereon adapted to clip said rearward panel on the temple bar, and an inwardly extending flange at the forward edge of said forward panel, the flange extending in front of the frame at the side thereof from the bar to which the shield is applied, said flange being of such width and so configured as not to interfere with the user's vision, and adapted to hold the shield against rearward movement on the temple bar when the bar is in position extending from the frame, said flange being adapted to move out from in front of the frame when the bar is swung closed.

2. A shield as set forth in claim 1 wherein said plate member and said flange have an upper edge, and wherein the shield further comprises an upper protection plate extending between the upper edge of the plate member and the upper edge of the inwardly extending flange for shielding the user's eye from debris falling from above.

3. A shield as set forth in claim 2 wherein the upper protection plate extends from the rearward edge of the transition panel to said inwardly extending flange and wherein the upper protection plate includes an inner edge adapted to correspond generally to the contour of the user's face.

4. A shield as set forth in claim 1 wherein said plate member further comprises a bottom margin extending from the rearward panel to the forward panel, said bottom margin being positioned below the eye socket of the wearer and constructed to flare outwardly away from the user's face for distributing the force encountered upon an impact with an object to an area below the eye socket.

5. A shield as set forth in claim 4 wherein said rearward panel extends rearwardly to a position posterior of the eye socket for distributing the force encountered upon an impact with a foreign object to an area behind the eye socket.

6. A shield as set forth in claim 1 wherein said plate member is transparent.

7. A shield as set forth in claim 6 wherein said forward generally flat panel extends rearwardly a sufficient distance to permit clear peripheral vision for the user.

8. A shield as set forth in claim 1 wherein said clip means comprises a clip adapted to clip said rearward panel on the temple bar.

9. A shield as set forth in claim 8 wherein said clip comprises a top wall portion extending laterally outwardly from the rearward panel and a resilient leg portion extending downwardly from the top wall portion to define with said top wall and said side plate an aperture adapted to receive the temple bar, and wherein the aperture of the clip is co-linearly positioned with respect to the opening of the transition panel to enable the shield to be mounted to any spectacle having a temple bar.

10. A shield for application to a temple bar of spectacles comprising a frame and left and right temple bars each pivotally interconnected at one end constituting its forward end to the frame at a respective side of the frame, said shield as applied to a temple bar at one side of the spectacles functioning to shield the user's eye at that side, said shield comprising an elongate relatively thin rigid plastic plate member which as applied to a temple bar lies generally flat against the respective side of the user's head extending between the frame and the respective ear of the user, said plate member having a forward generally flat panel having a forward edge and a rearward edge and positionable on the outside of the temple bar, an intermediate generally flat transition panel angled rearwardly and inwardly from the rearward edge of the forward panel and having an opening therein for the temple bar, said transition panel having a rearward edge which is adapted to extend on the inside of the respective temple bar as the shield is applied to its bar, and a rearward generally flat panel extending rearward from the rearward edge of the intermediate transition panel and adapted to extend on the inside of the temple bar as the shield is applied to the bar, said rearward panel having a clip thereon adapted to clip said rearward panel on the temple bar, an inwardly extending flange at the forward edge of said forward panel, the flange extending in front of the frame at the side thereof from the bar to which the shield is applied, said flange being of such width and so configured as not to interfere with the user's vision, and adapted to hold the shield against rearward movement on the temple bar when the bar is in position extending from the frame, said flange being adapted to move out from in front of the frame when the bar is swung closed, and an upper protection plate extending between the top edge of the plate member and the top edge of the inwardly extending flange, the upper protection plate including an inner edge adapted to correspond generally to the contour of the user's face for shielding the user's eye from debris falling from above.

11. A shield as set forth in claim 10 wherein said rearward panel extends rearwardly to a position posterior of the eye socket and wherein said plate member further comprises a bottom margin extending from the rearward panel to the forward panel, said bottom margin being positioned below the eye socket of the wearer and constructed to flare outwardly away from the user's face for distributing the force encountered upon an impact with an object to an area below and behind the eye socket.

12. A shield as set forth in claim 10 wherein said plate member is transparent and wherein said forward generally flat panel of the plate member extends rearwardly a sufficient distance to permit clear peripheral vision for the user.

13. A shield as set forth in claim 10 wherein said clip comprises a top wall portion extending outwardly from the rearward panel and a resilient leg portion extending downwardly from the top wall portion to define with said top wall and said side plate an aperture for receiving the temple bar, said aperture being co-linearly positioned with respect to the opening of the transition panel to enable the shield to be mounted to any temple bar.

* * * * *